(12) United States Patent
Mukai et al.

(10) Patent No.: US 12,097,275 B2
(45) Date of Patent: *Sep. 24, 2024

(54) HAIR COLORING METHOD

(71) Applicant: SUNNYPLACE CO., LTD., Tokyo (JP)

(72) Inventors: Nobuhito Mukai, Taito-ku (JP); Takashi Mukai, Taito-ku (JP)

(73) Assignee: SUNNYPLACE CO., LTD., Tokyo (JP)

( * ) Notice: Subject to any disclaimer, the term of this patent is extended or adjusted under 35 U.S.C. 154(b) by 718 days.

This patent is subject to a terminal disclaimer.

(21) Appl. No.: 17/286,385

(22) PCT Filed: Dec. 18, 2018

(86) PCT No.: PCT/JP2018/046657
§ 371 (c)(1),
(2) Date: Apr. 16, 2021

(87) PCT Pub. No.: WO2020/079858
PCT Pub. Date: Apr. 23, 2020

(65) Prior Publication Data
US 2021/0346268 A1 Nov. 11, 2021

(30) Foreign Application Priority Data
Oct. 18, 2018 (JP) .................. 2018-197060

(51) Int. Cl.
*A61Q 5/10* (2006.01)
*A61K 8/20* (2006.01)
(Continued)

(52) U.S. Cl.
CPC .............. *A61K 8/4946* (2013.01); *A61K 8/20* (2013.01); *A61K 8/342* (2013.01); *A61K 8/39* (2013.01);
(Continued)

(58) Field of Classification Search
CPC ........ A61K 8/4946; A61K 8/20; A61K 8/342; A61K 8/39; A61K 8/44; A61K 8/447;
(Continued)

(56) References Cited

U.S. PATENT DOCUMENTS 11,065,185 B2 * 7/2021 Mukai .................. A61K 8/416
11,083,681 B2 * 8/2021 Mukai .................. A61K 8/4946
(Continued)

FOREIGN PATENT DOCUMENTS

JP H11-501947 2/1999
JP 2012-171952 9/2012
(Continued)

OTHER PUBLICATIONS

Search Report and Written Opinion received in International Application No. PCT/JP2018/046657; Mar. 19, 2019.

*Primary Examiner* — Eisa B Elhilo
(74) *Attorney, Agent, or Firm* — ALG Intellectual Property, LLC

(57) ABSTRACT

A hair coloring method may include a step of applying a mixture of the following (A) and (B) in a predetermined ratio: (A) a hair coloring agent comprising at least a basic dye, a HC dye, a second amino acid, a first cationic surfactant, a thickener, an oil agent, a first pH adjusting agent, a wetting agent and at least one selected from the group consisting of thioglycolic acid, cysteine, 3-mercapto-1,2-propanediol, cysteamine, and derivatives and salts thereof, wherein the pH of the hair coloring agent is pH 3.5 or higher, and (B) a hair cosmetics comprising at least an alkaline agent, a first amino acid, higher alcohols having 12 to 22 carbon atoms, a surfactant, and a thickener. The hair coloring method may further include a step of providing a predetermined time after the application.

10 Claims, 9 Drawing Sheets

(51) Int. Cl.
*A61K 8/34* (2006.01)
*A61K 8/39* (2006.01)
*A61K 8/44* (2006.01)
*A61K 8/46* (2006.01)
*A61K 8/49* (2006.01)

(52) U.S. Cl.
CPC .............. *A61K 8/44* (2013.01); *A61K 8/447* (2013.01); *A61K 8/46* (2013.01); *A61K 8/463* (2013.01); *A61Q 5/10* (2013.01); *A61K 2800/48* (2013.01); *A61K 2800/52* (2013.01); *A61K 2800/884* (2013.01)

(58) Field of Classification Search
CPC ...... A61K 8/46; A61K 8/463; A61K 2800/48; A61K 2800/52; A61K 2800/884; A61K 8/37; A61K 8/375; A61K 8/411; A61K 8/416; A61K 8/418; A61K 8/42; A61K 2800/882; A61K 8/922; A61K 8/19; A61K 8/22; A61K 8/41; A61K 2800/43; A61Q 5/10; A61Q 5/065
USPC .................................................................. 8/405
See application file for complete search history.

(56) References Cited

U.S. PATENT DOCUMENTS 11,351,100 B2 * 6/2022 Mukai ...................... A61K 8/37
2016/0128915 A1 * 5/2016 Konno ................ B65D 83/752
8/406

FOREIGN PATENT DOCUMENTS

| JP | 2017-31085 | 2/2017 | |
|---|---|---|---|
| JP | 2017-88502 | 5/2017 | |
| WO | WO-2016/166201 | 10/2016 | |
| WO | WO 2016166201 A1 * | 10/2016 | ............... A61Q 5/05 |

\* cited by examiner

[Figure 1]

| Display name | | Molecular weight | INCI name | 3-mercapto-1,2-propanediol 0% | 3-mercapto-1,2-propanediol 1% | 3-mercapto-1,2-propanediol 3% |
|---|---|---|---|---|---|---|
| basic | Red51 | 279.775 | Basic Red 51 | | | |
| | Brown16 | 356.857 | Basic Brown 16 | | | |
| | Brown17 | 401.854 | Basic Brown 17 | | | |
| | Blue75 | 516.177 | Basic Blue 75 | | | |
| | Blue77 | 495.337 | Basic Blue 77 | | | |
| | Blue99 | 451.752 | Basic Blue 99 | | | |
| | Violet2 | 365.91 | Basic Violet 2 | | | |
| | Yellow57 | 371.872 | Basic Yellow 57 | | | |

[Figure 2]
| | | |
|---|---|---|
| a) | 3-mercapto-1,2-propanediol 0% Formulation<br>Basic Brown 16 0.2%, Basic Blue 77 0.2% | 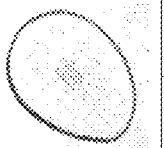 |
| b) | 3-mercapto-1,2-propanediol 0.5% Formulation<br>Basic Brown 16 0.2%, Basic Blue 77 0.2% | 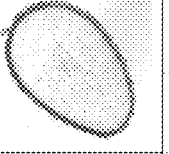 |
| c) | 3-mercapto-1,2-propanediol 1.0% Formulation<br>Basic Brown 16 0.2%, Basic Blue 77 0.2% | 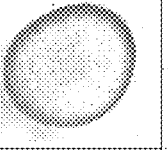 |
| d) | 3-mercapto-1,2-propanediol 3.0% Formulation<br>Basic Brown 16 0.2%, Basic Blue 77 0.2% | 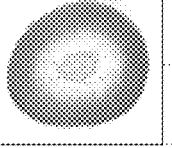 |

[Figure 3]

| | | |
|---|---|---|
| a) | 3-mercapto-1,2-propanediol 0% Formulation<br>Basic Brown 16 0.2%, Basic Blue 77 0.2% | 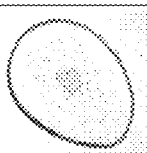 |
| b) | 3-mercapto-1,2-propanediol 0.5% Formulation<br>Basic Brown 16 0.2%, Basic Blue 77 0.2% |  |
| c) | 3-mercapto-1,2-propanediol 1.0% Formulation<br>Basic Brown 16 0.2%, Basic Blue 77 0.2% | 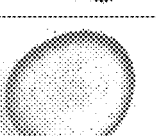 |
| d) | 3-mercapto-1,2-propanediol 3.0% Formulation<br>Basic Brown 16 0.2%, Basic Blue 77 0.2% |  |
| e) | 3-mercapto-1,2-propanediol 4.0% Formulation<br>Basic Brown 16 0.2%, Basic Blue 77 0.2% | 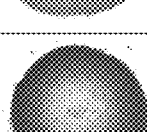 |
| f) | 3-mercapto-1,2-propanediol 5.0% Formulation<br>Basic Brown 16 0.2%, Basic Blue 77 0.2% | 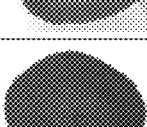 |
| g) | 3-mercapto-1,2-propanediol 10.0% Formulation<br>Basic Brown 16 0.2%, Basic Blue 77 0.2% |  |

[Figure 4]

[Table 1]

| | Abbreviation or Product name | Components(Display name) | Manufacturer | Compounding amount (% by mass) |
|---|---|---|---|---|
| Water phase | | Water | | Residue |
| | Concentrated glycerin for cosmetic | Glycerin | Sakamoto Pharmaceutical Co., Ltd. | 1.00 |
| | 1,3-butylene glycol-P | BG | KH N eochem Co. Ltd. | 1.00 |
| | | Pentylene glycol | | 1.00 |
| | | Hydroxyethyl cellulose | | 0.25 |
| | | Thioglycerin | Asahi Kagaku Kogyo Co., Ltd. | 0.10 |
| | Catinal STB-70 | Steartrimonium bromide | Toho Chemical Industry Co., Ltd. | 1.50 |
| | | Isopropanol | | 1.00 |
| Oil phase | KALCOL 4098 | Myristyl alcohol | Kao Corporation | 5.00 |
| | Lanette 22 | Behenyl alcohol | BASF Japan Co., Ltd. | 1.00 |
| | Cegesoft C24 | Ethylhexyl palmitate | BASF Japan Co., Ltd. | 2.00 |
| | Cutina CP | Cetyl palmitate | BASF Japan Co., Ltd. | 1.00 |
| | | Glycol stearate | | 2.00 |
| | Refined shea butter | Shea fat | Koei Kogyo Co., Ltd. | 1.00 |
| Alkaline agent | | Ammonium hydrogen carbonate | | 1.00 |
| Emulsification stable / viscosity imparting ingredient | Hisolve EPH | Phenoxyethanol | Toho Chemical Industry Co., Ltd. | 0.60 |
| | L-Menthol | Menthol | K. Kobayashi & Co., Ltd. | 0.10 |
| | Dehydrated ethanol | Ethanol | Kenei Pharmaceutical Co., Ltd. | 1.00 |
| Anti-inflammatory ingredient | Dipotassium glycyrrhizinate | Glycyrrhizic acid 2K | Maruzen Pharmaceutical Co., Ltd. | 0.10 |
| Antiallergic ingredient | Pomegranate seed extract BG -100 | Pomegranate seed extract | Koei Kogyo Co., Ltd. | 0.50 |
| Pigment | | Basic blue 99 | | 0.30 |
| | | Basic brown 16 | | 0.50 |
| | | HC blue 2 | | 0.60 |
| | | HC yellow 4 | | 0.20 |
| | | HC yellow 2 | | 0.10 |
| Amino acid group | L-Arginine | Arginine | Kyowa Hakko Bio Co., Ltd. | 0.10 |
| | L-histidine hydrochloride monohydrate | Histidine HCl | Wako Pure Chemical Industries, Ltd. | 0.02 |
| | L-lysine hydrochloride | Lysine HCl | Wako Pure Chemical Industries, Ltd. | 0.02 |
| Tolat (% by mass) | | | | 100.00 |
| pH | | | | 8.00 |

[Figure 5]

[Table 2]

| | Abbreviation or Product name | Components | Manufacturer |
|---|---|---|---|
| | Purified water | | |
| Alkaline agent | Reagent grade 25% Ammonia water | 25% Ammonia water | Osaka Sasaki Chemical Co., Ltd. |
| Amino acid group | CSKE-200 | L-Cysteine hydrochloride | Osaka Sasaki Chemical Co., Ltd. |
| | L-Arginine | L-Arginine | Wako Pure Chemical Industries, Ltd. |
| | L-Histidine | L-Histidine | Wako Pure Chemical Industries, Ltd. |
| Antiallergic component | Pomegranate seed extract BG-100 | Pomegranate seed extract | KOEI KOGYO Co.,Ltd |
| Common ingredients | Concentrated glycerin for cosmetic | Concentrated glycerin | Sakamoto Pharmaceutical Co., Ltd. |
| | SILK-1000 | Hydrolyzed silk | Seiwa Kasei Co., Ltd. |
| | Kohtamin 60W | Cetyltrimethylammonium chloride | Kao Corporation |
| | — | Fragrance | Kotobuki Fragrance Co., Ltd. |
| Emulsifying stability and viscosity-imparting | EMACOL VS | Cetyl alcohol<br>Lauryl alcohol<br>Polyoxyethylene oleyl ether<br>Polyoxyethylene lauryl ether<br>Sodium lauryl sulfate | Sanei Chemical Co., Ltd. |

[Figure 6]
[Table 3]

| | | Components(Display name) | Compounding amount |
|---|---|---|---|
| A phase | Base | Water | Residue |
| | Alkaline agent | Ammonia water | 2.40 |
| | Amino acid group | Cysteine HCl | 1.00 |
| | | Arginine | 1.00 |
| | | Histidine | 1.00 |
| B phase | Antiallergic component | Pomegranate seed extract | 0.0025 |
| | Common ingredients | Glycerin | 1.00 |
| | | Hydrolyzed silk | 0.50 |
| | | Cetyltrimethylammonium chloride | 1.50 |
| | | Fragrance | 0.20 |
| C phase | Emulsifying stability and viscosity-imparting ingredients | Cetyl alcohol | 1.92 |
| | | Lauryl alcohol | 0.24 |
| | | Polyoxyethylene oleyl ether | 0.39 |
| | | Polyoxyethylene lauryl ether | 0.27 |
| | | Sodium lauryl sulfate | 0.18 |
| | | Total(% by mass) | 100.00 |
| | | pH | 10.38 |

[Figure 7]
[Table 4]

| Abbreviation or Product name | Components | Manufacturer |
|---|---|---|
| Sodium bromate | Sodium bromate | KANTO CHEMICAL CO., INC. |
| Chitofilmer | Hydroxypropyl Chitosan solution | ICHIMARU PHARCOS Co., Ltd. |
| Pomegranate seed extrac BG-100 | Pomegranate seed extrac | KOEI KOGYO Co.,Ltd. |
| Citric acid | Citric acid | Showa Kako Corporation |
| L-Histidine monohydrochloride monohydrate | L-Histidine monohydrochloride | Wako Pure Chemical Industries, Ltd. |
| L-Arginine hydrochloride | L-Arginine hydrochloride | KYOWA HAKKO BIO CO.,LTD. |
| Kohtamin 24P | Lauryl trimethyl ammonium chloride solution | Kao Corporation |
| Genagen CAB818J | Coconut oil fatty acid amide propyl betaine liquid | Clariant Japan K.K. |

[Figure 8]

[Table 5]

| | | Components(Display name) | Compounding amount |
|---|---|---|---|
| A phase | | Water | Residue |
| | Oxidant | Sodium bromate | 8.00 |
| | Chitosan derivative | Hydroxypropyl chitosan | 0.10 |
| | Antiallergic component | Pomegranate seed extract | 0.0025 |
| | Basic amino acid derivative | Histidine HCl | 0.05 |
| | | Arginine HCl | 0.05 |
| | pH adjuster | Citric acid | q.s. |
| B phase | Cationic surfactant | Lauryl trimethyl ammonium chloride solution | 0.27 |
| C phase | Amphoteric surfactant | Cocamidopropyl betaine | 1.50 |
| | | Total(% by mass) | 100.00 |
| | | pH | 6.67 |

[Figure 9]

[Table 6]

| Components | Formulation of Example 2 | | | |
|---|---|---|---|---|
| | a) | b) | c) | d) |
| Purified water | Amount to be 100 in total | | | |
| 3-mercapto-1,2-propanediol | 0 | 0.5 | 1 | 3 |
| Coconut oil fatty acid amide propyl betaine solution | 5 | 5 | 5 | 5 |
| Basic Brown 16 | 0.2 | 0.2 | 0.2 | 0.2 |
| Basic Blue 77 | 0.2 | 0.2 | 0.2 | 0.2 |
| 25% of ammonia water | q.s. | q.s. | q.s. | q.s. |
| pH | 10.403 | 9.874 | 9.461 | 8.994 |

[Figure 10]

[Table 7]

| Components | % |
|---|---|
| Purified water | 98 |
| N-coconut oil fatty acid acyl-L-glutamic acid triethanolamine solution | 1.5 |
| Phenoxyethanol | 0.5 |

[Figure 11]

[Table 8]

| Prescription | Number of washing | L* | a* | b* |
|---|---|---|---|---|
| 3-mercapto-1,2-propanediol 0% formulation of Example 2 a) | 0 | 21.12 | 8.02 | 5.5 |
| | 10 | 29.52 | 11.28 | 9.26 |
| | 20 | 36.11 | 11.79 | 10.56 |
| 3-mercapto-1,2-propanediol 0.5% formulation of Example 2 b) | 0 | 19.23 | 3.06 | 2.94 |
| | 10 | 24.13 | 7.3 | 6.17 |
| | 20 | 25.35 | 5.75 | 4.83 |
| 3-mercapto-1,2-propanediol 1.0% formulation of Example 2 c) | 0 | 18.20 | 2.16 | 1.3 |
| | 10 | 22.07 | 3.67 | 4.56 |
| | 20 | 24.19 | 7.46 | 5.42 |
| 3-mercapto-1,2-propanediol 3.0% formulation of Example 2 d) | 0 | 17.66 | 0.9 | 1.23 |
| | 10 | 20.01 | 0.82 | -0.28 |
| | 20 | 19.15 | 1.5 | -0.69 |

[Figure 12]

[Table 9]

| Components | Formulation | | |
|---|---|---|---|
| | e) | f) | g) |
| Purified water | Amount to be 100 in total | | |
| 3-mercapto-1,2-propanediol | 4 | 5 | 10 |
| Coconut oil fatty acid amide propyl betaine solution | 5 | 5 | 5 |
| Basic Brown 16 | 0.2 | 0.2 | 0.2 |
| Basic Blue 77 | 0.2 | 0.2 | 0.2 |
| 25% of ammonia water | q.s. | q.s. | q.s. |
| pH | 8.792 | 8.759 | 8.474 |

HAIR COLORING METHOD

TECHNICAL FIELD

The present invention relates to a hair coloring method, and in particular, relates to a hair coloring method using a mixture of a hair cosmetic composition and a hair coloring agent composition capable of hardly damaging hair, reducing skin damage, and having a property of keeping color quality and penetrating dyeing power.

BACKGROUND ART

As hair coloring, there are mainly hair color, which is a permanent hair dye for quasi drugs, and hair manicure and hair color treatment, which are semi-permanent hair dyes for cosmetics. In particular, the hair colors of permanent hair dyes containing paraphenylene diamine (oxidative dye) is mainstream, but in the case of black-based dark colors, since the amount of diamine-based compounds increases. More attention is required.

For example, as a hair coloring composition comprising paraphenylenediamine (oxidative dye), a hair coloring composition characterized by comprising (a) a water-soluble peroxygen bleach; (b) a bleaching aid selected from an organic peroxyacid bleach precursor and/or a preformed organic peroxyacid; and (c) one or more hair coloring agents is known (Patent literature 1).

PRIOR ART LITERATURE

Patent Literature

Patent literature 1: JP-A1-H11-501947

DISCLOSURE OF THE INVENTION

Problems to be Resolved by the Invention

However, in the prior art including the above-mentioned Patent literature 1, those containing paraphenylene diamine (oxidative dye) have a larger amount of diamine based compound in the case of a dark black color as described above. In addition to this, in recent years, skin disorders have been reported due to the use of a substance called paraphenylenediamine (oxidative dye).

In addition, the hair manicure of semi-permanent hair dye is characterized in that the color (acidic dye) penetrates into the inside of hair after a single use and the hair manicure has a feature of a color lasting for 2 to 3 weeks. However, the longer it is left on the scalp, the more difficult it is to remove the dye. Moreover, it is difficult for practitioner to apply to the edge of the hairline. Therefore, such hair dye tends to be avoided in salons and beauty salons because the operator's specific skill is needed and the dyeing is worse than the hair color.

On the other hand, in the above-mentioned hair color, it is possible to dye even cortex (hair cortex. inside hair), but in hair color treatment, since it is aimed that the cuticle (hair skin) and cortex near the hair surface are dyed, in some cases, there was problem that it was not possible to achieve a hair color that has a sufficient property of keeping color quality.

Therefore, the object of the present invention is to provide a hair coloring method that has a better property of keeping color quality, hardly damages hair, reduces skin damage and is free of paraphenylenediamine when performing hair dye.

Means of Solving the Problems

In order to achieve the above object, the present inventors have intensively studied the hair coloring method, and as a result, have found the present invention.

That is, a hair coloring method of the present invention is characterized in that it comprises a step of applying a mixture of the following (A) and (B) in a predetermined ratio, (A) a hair coloring agent comprising at least a basic dye, a HC dye, a second amino acid, a first cationic surfactant, a thickener, an oil agent, a first pH adjusting agent, a wetting agent and at least one selected from the group consisting of thioglycolic acid, cysteine, 3-mercapto-1,2-propanediol, cysteamine, and derivatives and salts thereof, wherein the pH of the hair coloring agent is pH 3.5 or higher, and, (B) a hair cosmetics comprising at least an alkaline agent, a first amino acid, higher alcohols having 12 to 22 carbon atoms, a surfactant, and a thickener, and, a step of providing a predetermined time after the application.

Further, in a preferred embodiment of the hair coloring method of the present invention, it is characterized in that the content of at least one component selected from the group consisting of thioglycolic acid, cysteine, 3-mercapto-1,2-propanediol, cysteamine, and derivatives and salts thereof is 0.01 to 10.0% by weight based on the total amount of the hair coloring agent.

Further, in a preferred embodiment of the hair coloring method of the present invention, it is characterized in that it further comprises a step of applying the cuticle care agent after the application.

Further, in a preferred embodiment of the hair coloring method of the present invention, it is characterized in that the cuticle care agent comprises a second cationic surfactant, a second pH adjuster, and at least one selected from sodium bromate and hydrogen peroxide.

Further, in a preferred embodiment of the hair coloring method of the present invention, it is characterized in that it further comprises a step of leaving it for a certain period of time after applying the cuticle care agent.

Further, in a preferred embodiment of the hair coloring method of the present invention, it is characterized in that a blending ratio of the (A) hair coloring agent and the (B) hair cosmetic to be mixed is (A)/(B)=1 to 20.

Further, in a preferred embodiment of the hair coloring method of the present invention, it is characterized in that the alkaline agent is at least one selected from aqueous ammonia, ammonium carbonate, sodium carbonate, ethanolamines, ammonium hydrogencarbonate, and arginine.

Further, in a preferred embodiment of the hair coloring method of the present invention, it is characterized in that the first or second amino acid is at least one selected from cysteine, arginine, lysine, histidine, and salts thereof.

Further, in a preferred embodiment of the hair coloring method of the present invention, it is characterized in that at least one of the hair coloring agent, the hair cosmetic, and the cuticle care agent comprises an antibody production inhibitor.

Further, in a preferred embodiment of the hair coloring method of the present invention, it is characterized in that the hair is heated in the step of providing a predetermined time after the application.

Effect of Invention

According to the hair color method of the present invention, it has advantageous effects that since it does not contain paraphenylenediamine, in addition to reducing the risk of rash and contact dermatitis, it is difficult to damage the hair even when the use period of the hair color is long. Also, it has advantageous effects that it keeps a good color tone (having a property of keeping color quality) and that it is possible for the practitioner to provide hair coloring to the new part without worrying about adhesion to the scalp.

Further, according to the hair coloring method of the present invention, the use of a specific component has an advantageous effect that the permeability is good and the amount of dyeing agent or the like can be reduced.

BRIEF DESCRIPTION OF THE DRAWINGS

FIG. 1 shows the observation results by an optical microscope of hair cross-section samples treated in a 0%, 1%, and 3% solution of 3-mercapto-1,2-propanediol when various dyes were used.

FIG. 2 shows the observation results by an optical microscope of hair cross-section samples treated in a 0%, 0.5%, 1%, and 3% solution of 3-mercapto-1,2-propanediol when 0.2% of Basic Brown 16 and 0.2% of Basic Blue 77 were mixed to make a dark brown color.

FIG. 3 shows the observation results by an optical microscope of hair cross-section samples treated in a 0%, 0.5%, 1%, 3%, 4%, 5% and 10% solution of 3-mercapto-1,2-propanediol when 0.2% of Basic Brown 16 and 0.2% of Basic Blue 77 were mixed to make a dark brown color.

FIGS. 4-12 depict Tables 1-9 showing various exemplary components, ingredients, examples, and/or methods that may be implemented according to principles described herein.

MODE FOR CARRYING OUT THE INVENTION

A hair coloring method of the present invention is characterized in that it comprises a step of applying a mixture of the following (A) and (B) in a predetermined ratio, (A) a hair coloring agent comprising at least a basic dye, a HC dye, a second amino acid, a first cationic surfactant, a thickener, an oil agent, a first pH adjusting agent, a wetting agent and at least one selected from the group consisting of thioglycolic acid, cysteine, 3-mercapto-1,2-propanediol, cysteamine, and derivatives and salts thereof, wherein the pH of the hair coloring agent is pH 3.5 or higher, and, (B) a hair cosmetics comprising at least an alkaline agent, a first amino acid, higher alcohols having 12 to 22 carbon atoms, a surfactant, and a thickener, and, a step of providing a predetermined time after the application.

It is preferable that the hair coloring agent comprises a basic dye, and an HC dye, a second amino acid, a first cationic surfactant, a thickener, an oil agent, a first pH adjuster, a wetting agent, and at least one selected from the group consisting of thioglycolic acid, cysteine, 3-mercapto-1,2-propanediol, cysteamine, and derivatives and salts thereof, and the hair coloring agent has a pH of 3.5 or higher. It is preferable that the hair cosmetic comprises an alkaline agent, a first amino acid, higher alcohols having 12 to 22 carbon atoms, a surfactant, and a thickener. This is because the present inventors have found that a formulation of thioglycerin (scientific name: 3-mercapto-1,2-propanediol) makes it possible to obtain a good hair dyeing even if the pH is not raised or heated, as compared with the hair dyed by raising the pH and heating without adding thioglycerin or the like.

First, a hair color agent composition and a hair color agent applicable to the present invention will be described below.

The hair coloring agent composition applicable to the present invention is characterized by comprising a basic dye, an HC dye, an amino acid, a cationic surfactant, a thickener, an oil agent, a pH adjuster, a wetting agent, and at least one selected from the group consisting of thioglycolic acid, cysteine, 3-mercapto-1,2-propanediol, cysteamine, and derivatives and salts thereof, wherein the pH of the hair coloring agent composition is pH 3.5 or more, from the viewpoint that when thioglycerin or the like is blended, hair dyeing having good robustness can be performed without raising the pH or heating. Further, in the hair color composition applicable to the present invention, an adjustment of the pH to 6.8 or more makes it possible to open the cuticle easily, and at the same time, basic amino acids such as L-arginine, L-lysine, L-histidine, and salts thereof can be fed into the hair. As a result, a product can be capable of being used for coloring while supplementing and repairing basic amino acids that have leaked from the hair in the past (as a hair damage). That is, if the hair coloring agent composition of the present invention is applied, it is possible to open the cuticle, and as a result, it has an advantageous effect that a hair color which has a property of keeping color quality can be achieved.

Further, in the present invention, the reason for selecting at least one selected from the group consisting of thioglycolic acid, cystine, 3-mercapto-1,2-propanediol, cysteamine, and derivatives and salts thereof is as follows. This is because, by including these components, components such as dyes can be deeply penetrated into the hair, and even a small amount of dye can sufficiently realize hair color. Moreover, this is because, by including these components, it is possible to maintain the effect of the dye for a long period of time. In the present invention, among thioglycolic acid, cystine, 3-mercapto-1,2-propanediol, cysteamine, and derivatives and salts thereof, 3-mercapto-1,2-propanediol can be preferably used from the viewpoint of odor and crystal precipitation etc.

In addition, although the present invention does not require an alkaline agent and has an excellent dye penetration promoting action on hair even in the neutral region, in a preferred embodiment of the hair coloring agent composition applicable to the present invention, from the viewpoint of easy opening of the cuticle and adjusting pH to a predetermined value or more, as the pH adjusting agent mention may be made of at least one selected from citric acid, phosphoric acid, lactic acid, malic acid, ammonia water, ammonium hydrogencarbonate, ammonium carbonate, potassium hydroxide, sodium hydroxide, monoethanolamine, ammonium phosphate, sodium citrate, ammonium citrate, sodium lactate, potassium phosphate, sodium phosphate. From the viewpoint of being weakly alkaline and having little residue on the hair, preferably, as the pH adjuster, mention may be made of ammonium bicarbonate, sodium bicarbonate and the like.

In a preferred embodiment of the present invention, the content of at least one component selected from the group consisting of thioglycolic acid, cystine, 3-mercapto-1,2-propanediol, cysteamine, and derivatives and salts thereof may be 0.01 to 10.0% by weight, preferably 0.05 to 5.0% by weight, more preferably 0.1 to 3.0% by weight, to the total amount of the hair coloring agent, from the viewpoint of a composition that is hypoallergenic and has an excellent effect of promoting penetration into the hair, From the viewpoint of efficiently opening the cuticle and exhibiting good color retention, the pH value of the hair coloring agent composition of the present invention can be adjusted to preferably pH 3.5 or higher, more preferably pH 5 to 11, and even more preferably pH 6.8 to 10.

Further, in a preferred embodiment of the hair coloring agent composition applicable to the present invention, it is characterized in that the amino acid is at least one selected from cysteine, arginine, lysine, histidine and salts thereof. Further, the amount of amino acids is not particularly limited, but it can be preferably 0.01 to 0.5% by mass, more preferably 0.01 to 0.3% by mass, more preferably 0.02 to 0.2% by mass, based on the total amount of the composition, from the viewpoint of maintaining the moisturizing and softness of the hair.

Further, in a preferred embodiment of the hair coloring agent composition applicable to the present invention, it is characterized in that under the INCI (INCI: International Nomenclature of Cosmetic Ingredient) name, the basic dye is at least one selected from Basic Blue 3, Basic Blue 7, Basic Blue 9, Basic Blue 26, Basic Blue 75, Basic Blue 77, Basic Blue 99, Basic Blue 124, Basic Red 51, Basic Red 76, Basic Yellow 57, Basic Purple 2, Basic Brown 16 or basic brown 17. Moreover, INCI (INCI: International Nomenclature of Cosmetic Ingredient: International Nomenclature of Cosmetic Ingredient) is an international labeling name for cosmetic ingredients created by the International Nomenclature Committee (INC). Further, the amount of the basic dye is not particularly limited, but it can be preferably 0.0005 to 5% by mass, more preferably 0.01 to 3% by mass, even more preferably 0.1 to 1% by mass, based on the total amount of the composition, from the viewpoint that the dyeing power is not strong but the damage to the hair is small.

Further, in a preferred embodiment of the hair coloring agent composition applicable to the present invention, it is characterized in that under the INCI name, the HC dye is at least one selected from HC blue 2, HC blue 12, HC blue 14, HC Blue 15, HC Blue 16, HC Blue 18, HC Yellow 2, HC Yellow 4, HC Yellow 5, HC Red 1, HC Red 3, or HC Orange 1. Further, the amount of the HC dye is not particularly limited, but it can be preferably 0.0005 to 5% by mass, more preferably 0.01 to 3% by mass, and even more preferably 0.1 to 1.5% by mass, with respect to the total amount of the composition, from the viewpoint of exhibiting a deeper color because the HC dye dyes the inside of the hair.

Further, in a preferred embodiment of the hair coloring agent composition applicable to the present invention, from the viewpoint of further improving the touch given to the hair, the cationic surfactant is characterized by being a quaternary ammonium salt and/or a tertiary amine. In addition, in a preferred embodiment of the hair coloring agent composition of the present invention, the quaternary ammonium salt is characterized by being an alkyltrimethylammonium chloride solution, stearyltrimethylammonium chloride, or stearyltrimethylammonium bromide. Further, in a preferred embodiment, the tertiary amine is characterized by being stearic acid dimethylaminopropylamide, stearic acid diethylaminoethylamide, or behenamidopropyldimethylamine. Further, the amount of the cationic surfactant is not particularly limited, but from the viewpoint of improving the hair dyeing ability of the basic dye, it can be preferably 0.01 to 10% by mass, more preferably 0.1 to 5% by mass, and still more preferably 1 to 3% by mass, based on the total amount of the composition.

In addition, the hair color composition applicable to the present invention may contain a thickener, a wetting agent, an oil agent and the like. In the present invention, these thickeners and the like are not particularly limited as long as they do not depart from the effects of the present invention, and a known thicker can be used. As the thickener, from the viewpoint of product stability, for example, mention may be made of hydroxyethyl cellulose, xanthan gum, polyethylene glycol and the like. Further, the amount of the thickener is not particularly limited, but from the viewpoint of: improving the stability of the product, it can be preferably 0.05 to 0.8% by mass, more preferably 0.1 to 0.5% by mass with, still more preferably, it can be 0.2 to 0.4 mass %, with respect to the total amount of the composition.

Also, as the wetting agent, mention may be made of glycerin, diglycerin, and 1,3-butylene glycol. Further, the amount of the wetting agent is not particularly limited, but from the viewpoint of easy application of the product, it can be preferably 0.1 to 15% by mass, more preferably 0.5 to 10% by mass, still more preferably 1 to 5% by mass, with respect to the total amount of the composition.

Also, as the oil agent, mention may be made of fats and oils, waxes, hydrocarbons, alkyl glyceryl ethers, esters, silicones, higher alcohols, and the like. Further, the amount of the oil agent is not particularly limited, but from the viewpoint of preventing the drying of the coating leaving time and the stability of the product, it can be preferably 1 to 30% by mass, more preferably 2 to 20% by mass, and still more preferably may be 3 to 15% by mass.

Further, the hair coloring agent applicable to the present invention is characterized by including the hair coloring agent composition applicable to the present invention as described above. The hair coloring agent composition applicable to the present invention can be appropriately included in the hair coloring agent as desired or depending on the use of the hair coloring agent.

In addition, an example of a hair cosmetic composition and a hair cosmetic applicable to the present invention will be described as follows.

The hair cosmetic composition applicable to the present invention is characterized by comprising an alkali agent, an amino acid, higher alcohols having 12 to 22 carbon atoms, a surfactant, and a thickener. It is not essential to add an alkaline agent, but it is possible to open the cuticle by adding an alkaline agent. That is, in hair coloring methods and the like, the cuticle (hair skin) and cortex near the hair surface are dyed, and there are cases where a hair color with sufficiently property of keeping a good color cannot be achieved. However, if the hair cosmetic composition is applied, it is possible to open the cuticle, and as a result, it has an advantageous effect that a hair color which has a property of keeping color quality can be achieved.

In other words, in the past, basic dyes and HC dyes dye cuticles and cortex close to the surface, but by using the hair cosmetic composition (swelling agent), the present inventors have found that it is possible to dye with basic dyes and HC dyes up to deeper parts of the hair.

From the viewpoint that the cuticle can be efficiently opened and the swelling effect can be satisfactorily exhibited, the pH value of the hair cosmetic composition of the present invention can be adjusted to preferably pH 3.5 or more, more preferably pH 5 to 11, and still more preferably pH 6.8 to 10. The amount of the alkali agent is not particularly limited, but from the viewpoint of efficiently opening the cuticle and exhibiting a good swelling effect, it can be preferably 0.1 to 3% by mass with respect to the total amount of the composition.

Moreover, the amount of the amino acid is not particularly limited, but from the viewpoint of keeping the moisture and flexibility of the hair, it can be set to preferably 0.01 to 0.5% by mass, more preferably 0.01 to 0.3%, and still more preferably 0.02 to 0.2% by mass, with respect to the total amount of the composition.

In the hair cosmetic composition applicable to the present invention, the higher alcohols having 12 to 22 carbon atoms is not particularly limited, but from the viewpoint of imparting smoothness to the hair, improving the emulsion stability, and adjusting the viscosity, mention may be made of cetyl alcohol, lauryl alcohol, myristyl alcohol, cetostearyl alcohol, stearyl alcohol, and behenyl alcohol and the like.

Further, the amount of the higher alcohols having 12 to 22 carbon atoms is not particularly limited, but from the viewpoint of imparting smoothness to hair, improving emulsification stability and adjusting the viscosity, preferably, the content can be 0.1 to 5.0% by mass, more preferably 0.1 to 3.0% by mass, and still more preferably 0.2 to 2.0% by mass.

In a preferred embodiment, the alkaline agent is not particularly limited, and examples thereof can include at least one selected from ammonia water, ammonium carbonate, sodium carbonate, ethanolamines, ammonium bicarbonate, and arginine. In a preferred embodiment of the hair cosmetic composition applicable to the present invention, the ethanolamine is characterized by being monoethanolamine, diethanolamine, and/or triethanolamine. Ethanolamines such as monoethanolamine are non-volatile and have little odor, but they remain highly on the hair and may hurt the hair. Further, arginine has a high affinity with hair, but it is weak regarding an action as an alkaline agent and has a mild reaction. Ammonia water has a pungent odor due to its volatility, but it is characterized by little residue on the hair and quick reaction. From this point of view, as the alkaline agent, mention may be made of preferably ammonia water.

Further, in a preferred embodiment, the amino acid may include at least one selected from cysteine, arginine, lysine, and/or histidine and these salts. Although it has been reported that arginine and histidine in the hair decrease with aging, in the present invention, it is possible for arginine, histidine hydrochloride, lysine hydrochloride blended in the hair cosmetic composition (swelling agent) of the present invention: to penetrate into the hair and exert a hair repair effect.

The hair cosmetic composition applicable to the present invention may contain a surfactant and a thickener. About these surfactant and a thickener, unless it deviates from the effect of this invention, it does not specifically limit and a well-known one can be used.

Further, in a preferred embodiment, in the hair cosmetic composition applicable to the present invention, the alkaline agent contained in the hair cosmetic composition can open the cuticle.

In addition, in order to tighten the cuticle etc., after performing hair color using the hair cosmetic composition applicable to the present invention, for example, it is also possible to apply a cuticle care agent including sodium bromate. It is also possible to dye the HC dye, which is easily fading, inside the hair in order to delay the color fading.

Further, a hair cosmetic applicable to the present invention is characterized by including the above-described hair cosmetic composition applicable to the present invention.

The above is an explanation of examples of hair cosmetics and hair coloring agents.

In the present invention, a mixture of these hair color agents and hair cosmetics in a predetermined ratio can be applied. The reason why both of the hair color agents and hair cosmetics are mixed is that the present inventors have found that, when they are used as a mixture, they are deeply dyed and have good color retention, as compared with the case where they are used alone. It suffices to mix both, and the predetermined ratio is not particularly limited, but in a preferred embodiment, it is characterized in that the compounding ratio for mixing the (A) hair coloring agent and the (B) hair cosmetic is (A)/(B)=1 to 20. That is, from the viewpoint of hair dyeing power, the blending ratio of the hair coloring agent and the hair cosmetic can be preferably 1 to 20:1 by mass ratio, more preferably 5 to 15:1 by mass ratio, and further preferably 8 to 12:1 by mass ration.

Further, in the present invention, from the viewpoint that the cuticle can be efficiently opened, the swelling effect can be satisfactorily exhibited, and the dyeing can be advanced, a predetermined time can be provided after the application. Further, in a preferred embodiment of the hair coloring method of the present invention, in the step of providing a predetermined time after the application, the hair is warmed from the viewpoint of enhancing the permeation dyeing power. The warming time is also not particularly limited if desired, but from the viewpoint of efficiently dyeing hair, it can be 1 to 60 minutes, preferably 5 to 40 minutes. From the viewpoint of the treatment process time, the temperature may be raised to about 40° C. in about 10 minutes to (about 10 minutes or more) and kept at the temperature for about 30 minutes. Further, in a preferred embodiment of the hair coloring method of the present invention, the application portion may be covered with a wrap and warmed using a hair dryer heat cap during the time for leaving the hair with application.

Further, the present invention may include a step of applying a cuticle care agent after the predetermined time. In addition, in a preferred embodiment of the hair coloring method of the present invention, the present invention may include a step of leaving for a certain time, from the viewpoint that the cuticle (hair scalp) that has been opened is tightened and dyeing the HC dye inside the hair, after the cuticle care agent is applied. Although the standing time is not particularly limited, for example, the standing time can be 1 to 20 minutes, preferably 1 to 10 minutes.

In addition, in a preferred embodiment of the hair coloring method of the present invention, a step of applying a cuticle care agent may be further included. For example, in a preferred embodiment of the hair coloring method of the present invention, after the hair cosmetic composition and the hair coloring agent are mixed and applied, a step of applying a cuticle care agent containing at least one selected from sodium bromate and hydrogen peroxide, a second cationic surfactant and a second pH adjusting agent may be included. Moreover, as the second pH adjuster, an acidic pH adjuster can be blended. Further, from the viewpoint of returning to a healthy hair condition (isoelectric band pH 4.5 to 5.5), as the pH adjusting agent, mention may be made of organic acids such as citric acid, phosphoric acid, phytic acid, lactic acid, malic acid, and acidic amino acids such as glutamic acid and the like.

Further, in a preferred embodiment of the hair coloring method of the present invention, the amino acid is characterized by being at least one selected from cysteine, arginine, lysine, or histidine. As to the amino acid, reference may be made to the above descriptions in the hair cosmetics etc., applicable to the present invention as mentioned above.

Further, in a preferred embodiment of the hair coloring method of the present invention, the first or second amino acid is characterized by being at least one selected from cysteine, arginine, lysine, or histidine and these salts. As to the first or second amino acid, reference may be made to the above descriptions in the hair cosmetics and hair coloring agent etc., applicable to the present invention as mentioned above.

Further, in a preferred embodiment of the hair coloring method of the present invention, the hair coloring method may further include a step of applying a shampoo agent. When applying a shampoo agent to hair, from a viewpoint of removing obstruction factors, such as hairdressing agents and sebum, it may be applied before the treatment of hair cosmetics. In this case, as the shampoo agent, preferably, estrone shampoo, estrone black, applecel shampoo premium, nanosupple cleansing shampoo and the like (manufacturer and distributor of these products: Sunny Place Co., Ltd.) can be used.

The shampoo agent may also be applied after coloring. In this case, the pH of the shampoo agent is preferably weakly acidic. Further, as the shampoo agent, estrone shampoo or applecel shampoo premium (shampoo agent, manufacturer and distributor: Sunny Place Co., Ltd.) can be preferably used.

Further, in a preferred embodiment of the hair coloring method of the present invention, at least one of the hair coloring agent, the hair cosmetic, and the cuticle care agent may further contain an antibody production inhibitor. As the antibody production inhibitor, from the viewpoint of prevention and improvement of allergic diseases, mention may be made of pomegranate seed extract, mushrooms extract belonging to the genus agaricus, etc., willow mint extract, edelweiss extract and the like.

For example, the case where a pomegranate seed extract is used as an antibody production inhibitor will be described below as an example. Pomegranate seed extract is an extract derived from pomegranate seeds. The pomegranate seed extract applied to the present invention covers all pomegranate seed extracts as long as they are derived from pomegranate seeds.

Further, in a preferred embodiment, the pomegranate seed extract is characterized by containing punicic acid or ellagic acid. The pomegranate seed extract can be obtained, for example, by the following method. It is characterized in that at first, the crushed product obtained by crushing pomegranate seeds is immersed in at least one solvent selected from the group consisting of ethanol, methanol, water and hexane, the supernatant is separated to obtain the pomegranate seed extract. For example, it can be shaken and extracted. In shaking extraction, for example, extraction can be performed by setting the rotator in a low temperature room such as about 4° C. and rotating.

More specifically, first, pomegranate seeds are prepared. Pomegranate seeds are washed if necessary and dried. It is preferable to perform the drying sufficiently. This is because the subsequent pulverization is performed uniformly.

Next, the pomegranate seeds are crushed. The pulverization method is not particularly limited, and a known pulverizer such as a ball mill, a hammer mill, a roller mill, a rod mill, a sample mill, a stamp mill, a disintegrator, a mortar, and a blender with a cooling device can be used. Moreover, since it is considered that the pomegranate seed composition is decomposed due to the heat generated during the pulverization, the pulverization time can be set to several seconds and it can be repeated about a dozen of times.

Next, the pomegranate seeds are crushed to obtain a crushed product, and then the crushed product is immersed in various solvents. The solvent in this case is not particularly limited, and the solvent can be appropriately set according to the desired effect. Further, in a preferred embodiment of the method for producing a pomegranate seed extract of the present invention, the solvent is characterized in that the solvent is at least one selected from the group consisting of ethanol, methanol, hexane and water. The solvent may be a polar or nonpolar solvent such as ethanol, methanol, water, hexane, ethyl acetate, chloroform or acetone. Preferably, methanol, ethanol and water, etc. can be mentioned.

Immersion can be performed under gentle stirring. The pulverized product is dipped in various solvents to obtain various solutions. Various solutions may be stirred depending on the state of the solution, and the solution may be left as it is depending on the case. The stirring is not particularly limited, but the stirring can be continued for 10 hours to 48 hours, preferably about 1 day (24 hours).

Then, the pomegranate seed extract can be obtained by separating the supernatant. If necessary, the supernatant is evaporated to dryness. Evaporation to dryness can be carried out using an evaporator on a warm bath at 20° C. to 60° C., preferably 37° C. to 40° C. By evaporating to dryness, the pomegranate seed extract can be stored for a long period of time.

The components contained in pomegranate seeds are sorted according to their physical properties by extracting pomegranate seeds with solvents having different polarities. Therefore, the type and content of the components of the pomegranate seed extract differ depending on the solvent used.

Moreover, an example of the hair coloring method of the present invention will be described below.
1) An appropriate pre-shampoo is performed to remove hair styling agents and stains.
2) A mixture of a hair color agent (containing a hair dye component) and a hair cosmetic (containing a basic cuticle swelling agent) applicable to the present invention in a predetermined ratio is applied to the hair by a brush.
3) The applied hair is covered with a plastic wrap to heat it with a hair dryer or a heat cap, and to leave it for about 30 minutes.
4) After 3), if necessary, the cuticle care agent is applied to the hair thoroughly and leave it for about 6 minutes.
5) After 4), a hair is washed with water at appropriate temperature and shampoo agent.
6) After towel drying, the hair is dried with a hair dryer.

EXAMPLE

As mentioned below, an embodiment of a hair coloring agent, and a cuticle care agent applicable to the present invention will be concretely explained in more detail with reference to Examples, but the invention is not intended to be interpreted as being limited to the following Examples.

First, a hair coloring agent applicable to the present invention was prepared.

Regarding the alkaline agent (pH adjusting agent), from the viewpoint that it is weakly alkaline and skin irritation does not easily occur, in the example, a test was conducted using ammonium hydrogen carbonate as an example.

In addition, about 80% of human hair is composed of keratin proteins derived from amino acid, L-cysteine is an amino acid that is also abundant in the hair. Therefore, L-cysteine and its salts were tried for the purpose of keeping the hair moisturized and flexible. Typical basic amino acids include L-arginine, L-lysine and L-histidine, but these are known to flow out when damaged, and there was found that 0.01 to 0.5% by mass of basic amino acids and salts thereof are preferable.

Table 1 in FIG. 4 shows the components of an example of the hair coloring agent composition in one embodiment of the present invention.

The preparation method is as follows.

Preparation Method

1. The aqueous phase (water phase) of Table 1 is warmed to 75-77° C. with stirring.
2. The oil phase in Table 1 is stirred while heating to 77-79° C. to make it uniform.
3. The pigment is added to water phase heated to 75-77° C. to homogenize, the oil phase is add to the mixture to emulsify and stir until uniform.
4. The content is slowly cooled, and when the temperature of the content is 43° C. or lower, the preservative, the refreshing component, the antiinflammatory component, the amino acid group are added and stirred until uniform, and then cooled to 32° C. or lower.

Moreover, the following models and electrodes were used for pH measurement.

Model of pH meter: F-71 (Horiba, Ltd.)
pH meter electrode: Type 9615 (Horiba, Ltd.)

In addition, a hair colorant applicable to the present invention was actually prepared, and a color fading test was performed on the hair bundle. As a result, it was found that the hair coloring agent applicable to the present invention was extremely excellent in color fading.

Conventionally, when a hair coloring agent that does not contain paraphenylenediamine is applied and left as it is, although, the base color is a basic dye and HC dye, which are considered to be safer than oxidative dyes, since it was dyed on the hair, the color persistence after the hair dyeing was bad, and there was the fault that it was easy to lose color due to repeated shampooing. It was found that In contrast to conventional hair coloring agents, the hair coloring agent applied to the present invention not only the base color easily penetrates but also it can be applied from the new part to the hair tip without worrying about adhesion to the scalp because it does not contain an acidic dye.

Thus, in the hair coloring agent etc., applicable to the present invention, when performing hair dye, compared with conventional hair color and hair manicure, in the conventional method, there are problems that 1) if the hair is damaged by repeated dyeing, the hair strength is reduced and elasticity is lost to thin a hair (In the case of hair color of prior art), 2) if the scalp rash occurs, the rash part will stain and be difficult to remove (in the case of hair manicure of prior art). However, in the present invention, there is no problem of the above, it was found that hair cosmetics with good penetration and dyeing power can be provided. In other words, in the present invention, it has also been found that safety is provided in addition to color retention.

Next, a hair cosmetic applicable to the present invention was prepared.

Regarding alkaline agents, ammonia water, ammonium carbonate, sodium carbonate, triethanolamines such as mono, di, or triethanolamines, ammonium hydrogen carbonate, arginine, and the like are considered. However, ethanolamines such as monoethanolamine are non-volatile and have little odor, but they remain highly on the hair and may hurt the hair. In addition, arginine has a high affinity with hair, but it is weak as to an action as an alkaline agent and has a mild reaction. Aqueous ammonia is the irritating odor due to volatile, but has a property that it has little residue on the hair and reacts quickly.

In addition, about 80% of human hair is composed of keratin proteins derived from amino acid, L-cysteine is an amino acid that is also abundant in the hair. Therefore, L-cysteine and its salts were tried for the purpose of keeping the hair moisturized and flexible. Typical basic amino acids include L-arginine, L-lysine and L-histidine, but these are known to flow out when damaged, and there was found that 0.01 to 0.5% by mass of basic amino acids and salts thereof are preferable.

Table 2 in FIG. 5 shows the components of an example of the hair cosmetic composition in one embodiment of the present invention.

Table 3 in FIG. 6 shows an adjustment example relating to the component example of the hair cosmetic according to the embodiment of the present invention.

The preparation method is as follows.

Preparation Method

1. After confirming the dissolution of the amino acid group in the purified water of Phase A in Table 3, the alkaline agent is mixed uniformly.
2. Next, while stirring the A phase of Table 3, the B phase of Table 3 is added and mixed uniformly.
3. Add Phase C in Table 3 with moderate stirring and stir until uniform.

Moreover, the following models and electrodes were used for pH measurement.

Model of pH meter: F-71 (Horiba, Ltd.)
pH meter electrode: Type 9615 (Horiba, Ltd.)

Table 4 in FIG. 7 shows an example of ingredients of the cuticle care agent in one embodiment of the present invention. The cuticle care agent includes an action of improving the condition of the cuticle such as adjusting and tightening the cuticle. In other words, it is not limited to the action of adjusting and tightening.

Table 5 in FIG. 8 shows an example of an adjustment method relating to the cuticle care agent applicable to the present invention according to the embodiment of the present invention.

The preparation method of the cuticle care agent applicable to the present invention is as follows.

Preparation Method

1. The residue components of Phase A in Table 5 in the purified water are mixed uniformly.
2. Next, while stirring the A phase of Table 5, the B phase of Table 5 is added and mixed uniformly.
3. Add Phase C in Table 5 with moderate stirring and stir until uniform.

Moreover, the following models and electrodes were used for pH measurement.

Model of pH meter: F-71 (Horiba, Ltd.)
pH meter electrode: Type 9615 (Horiba, Ltd.)

Next, an example based on the present invention will be described.

Example 1

The penetration of major basic dyes applicable to the present invention was compared. A hair commercially available 100% untreated gray hair (product number: BS-C, manufactured by Burax Co., Ltd.) with a length of 30 cm was divided into three equal parts to obtain a hair sample to be dyed. For Basic Red 51, Basic Brown 16 and 17, 0.2% of the pigment was dissolved in purified water, and the pH was adjusted to alkaline using 25% of ammonia water (manufactured by Wako Pure Chemical Industries, Ltd.), and a 0%, 1% and 3% solution of 3-mercapto-1,2-propanediol (manufactured by Wako Pure Chemical Industries, Ltd.) as thioglycerin was prepared. The optimum value of alkalinity is around pH 7.5 to 10.0, but there are differences depending on the dye, and some dyes cause precipitation in the solution if the pH is raised too much. In addition, for Basic Blue 75, 77, 99, Basic Violet 2, and Basic Yellow 57, 0.7% of dye was dissolved in 5.0% of amide betaine type amphoteric tenside coconut oil fatty acid amide propyl betaine solution (product number: softazoline CPB-R, Kawaken Fine Chemicals Co., Ltd.) to improve dye solubility, and was dissolved in purified water, and the pH was adjusted to alkaline using 25% of ammonia water (manufactured by Wako Pure Chemical Industries, Ltd.), and a 0%, 1% and 3% solution of 3-mercapto-1,2-propanediol (manufactured by Wako Pure Chemical Industries, Ltd.) was prepared. A hair sample obtained by dividing one gray hair into three equal parts is dipped in a 0%, 1%, 3% solution of 3-mercapto-1,2-propanediol of each dye, and left for 30 minutes in a constant temperature bath at 40° C. to obtain a stained hair sample. The hair sample was freeze-embedded with PVA resin, and then a hair cross-section sample (section thickness: 10 μm) was prepared using a microtome. Then, they were placed on a slide glass as a sample for microscopic observation and compared with a microscope (FIG. 1).

As shown in FIG. 1, it is found that the degree of penetration of the dye into the hair sample is deepest in all the dyes in the case of 3% of 3-mercapto-1,2-propanediol (the range where the color is dark from the outer periphery of the cross section is the largest one). In particular, it was more clear that the dyes of Basic Brown 16 and Basic Blue 77 had good penetration.

Example 2

Using the dyes of Basic Brown 16 and Basic Blue 77, which had good penetration in Example 1, a hair commercially available 100% untreated gray hair (product number: BS-C, manufactured by Beaulax Co., Ltd) was left for 30 minutes in a constant temperature bath at 40° C. and the hair was dyed dark brown in the following formulation example (Table 6 in FIG. 9). The hair sample was freeze-embedded with PVA resin, and then a hair cross-section sample (section thickness: 10 μm) was prepared using a microtome. Then, they were placed on a slide glass as a sample for microscopic observation and compared with a microscope (FIG. 2).

Example 3

A hair commercially available 100% untreated gray hair (product number: BM-W-A, manufactured by Burax Co., Ltd.) with a weight of 1 g and a length of 10 cm was dyed using the formulation of Example 1, and the hair bundle was washed with the following washing liquid for 5 minutes using a desktop type of ultrasonic cleaner. An amino acid-based anionic surfactant N-coconut oil fatty acid acyl-L-glutamic acid triethanolamine solution (product number: Amino Surfact ACMT-L, manufactured by Asahi Kasei Finechem Co., Ltd.) was used as the cleaning solution. Table 7 in FIG. 10 shows the components of the cleaning solution.

Next, in order to quantify the color fading due to the number of times wherein the hair was washed, it was measured with a spectroscopic colorimeter (manufactured by Nippon Denshoku Industries Co., Ltd., device name: SD6000). Table 8 in FIG. 11 shows the colors (L*, a*, b*) of the number of washings of each formulation. Table 8 shows the results regarding discoloration due to the number of times wherein the hair was washed. The difference in color due to the number of times wherein the hair was washed was measured using lightness (L*) or the like. In Table 8, it is shown that L* is the brightness, and light and dark colors are quantified, and the smaller the value, the darker the color. It is shown that a* indicates that the larger the value, the more red the direction, and the smaller the value, the greener the direction. In addition, it is shown that b* indicates that if the value is large, it advances in the yellow direction, and if the value is small, it advances in the blue direction.

Therefore, when thioglycerin is 0%, it is recognized that the values of L*, a* and b* are increased by washing 20 times, so the blackness is reduced and the red and yellow are stronger, so the color is closer to brown. On the contrary, in the case of 3%, the values of L*, a*, and b* hardly move, indicating that there is almost no change even after 20 washes. Moreover, the closer the value of L* is to 0, the darker the value. From these results, it can be seen that according to the present invention, there is little decrease in lightness and very little discoloration due to washing hair.

Example 4

Using the dyes of Basic Brown 16 and Basic Blue 77, which had good penetration in Example 1, a hair commercially available 100% untreated gray hair (product number: BS-C, manufactured by Beaulax Co., Ltd) was left for 30 minutes in a constant temperature bath at 40° C. and the hair was dyed dark brown in the following formulation example (Table 9). Table 9 in FIG. 12 shows examples of ingredients and formulations at this time. The hair sample was freeze-embedded with PVA resin, and then a hair cross-section sample (section thickness: 10 μm) was prepared using a microtome. Then, they were placed on a slide glass as a sample for microscopic observation and compared with a microscope (FIG. 3). FIG. 3 shows the observation result by the optical microscope of the hair cross-section sample treated in 0%, 0.5%, 1%, 3%, 4% 5% and 10% solutions of 3-mercapto-1,2-propanediol when 0.2% of Basic Brown 16 and 0.2% of Basic Blue 77 were mixed to make a dark brown color.

From the above results, it was found that when thioglycerin or the like is blended, although a step of providing a predetermined time after application is necessary, it is possible to dye hair having good robust characteristics without raising the pH or heating. Moreover, it was also found that it is more effective to add thioglycerin or the like and to increase the heating and pH. It was found that in the case of the dyes Basic Blue 99 and Basic brown 16, it is possible to dye hair with better robustness as the pH is raised to around pH 10, while in the case of Basic Blue 77, as the pH is raised to pH 8 or higher, the pigment broke and the color changed, resulting in weak hair dyeing.

From the above, it was found that the addition of thioglycerin makes it easier for dyes to enter the hair when coloring hair.

INDUSTRIAL APPLICABILITY

According to the present invention, a coloring method that does not easily damage hair, can reduce skin disorders, and allows dyes to easily enter hair is easy to spread and has high industrial utility value.

The invention claimed is:

1. A hair coloring method comprising:
   a step of applying a mixture of the following (A) and (B) in a predetermined ratio:
   (A) a hair coloring agent comprising at least a basic dye, a HC dye, a second amino acid, a first cationic surfactant, a thickener, an oil agent, a first pH adjusting agent, a wetting agent and at least one component selected from the group consisting of thioglycolic acid, cysteine, 3-mercapto-1,2-propanediol, cysteamine, or derivatives and salts thereof, wherein the pH of the hair coloring agent is pH 3.5 or higher, and
   (B) a hair cosmetic comprising at least an alkaline agent, a first amino acid, higher alcohols having 12 to 22 carbon atoms, a surfactant, and a thickener, and
   a step of providing a predetermined time after the step of applying the mixture.

2. The hair coloring method according to claim 1, wherein content of the at least one component selected from the group consisting of thioglycolic acid, cysteine, 3-mercapto-1,2-propanediol, cysteamine, or derivatives and salts thereof is 0.01 to 10.0% by weight based on a total amount of the hair coloring agent.

3. The hair coloring method according to claim 1, further comprising a step of applying a cuticle care agent after the step of applying the mixture.

4. The hair coloring method according to claim 3, wherein the cuticle care agent comprises a second cationic surfactant, a second pH adjuster, and at least one selected from sodium bromate or hydrogen peroxide.

5. The hair coloring method according to claim 3, further comprising a step of leaving the cuticle care agent for a certain period of time after the step of applying the cuticle care agent.

6. The hair coloring method according to claim 1, wherein a blending ratio of the (A) hair coloring agent and the (B) hair cosmetic to be mixed is (A)/(B)=1 to 20.

7. The method according to claim 1, wherein the alkaline agent is at least one selected from aqueous ammonia, ammonium carbonate, sodium carbonate, ethanolamines, ammonium hydrogencarbonate, or arginine.

8. The method according to claim 1, wherein the first or second amino acid is at least one selected from cysteine, arginine, lysine, histidine, or salts thereof.

9. The method according to claim 3, wherein at least one of the hair coloring agent, the hair cosmetic, or the cuticle care agent comprises an antibody production inhibitor.

10. The method according to claim 1, wherein hair is heated in the step of providing the predetermined time after the step of applying the mixture.

* * * * *